United States Patent [19]

Cartwright

[11] 4,390,622
[45] Jun. 28, 1983

[54] NEISSERIA BACTERIA SPECIES IDENTIFICATION AND BETA LACTAMASE TESTING METHODS

[76] Inventor: Garry W. Cartwright, 2227 Flat Creek, Richardson, Tex. 75080

[21] Appl. No.: 303,725

[22] Filed: Sep. 21, 1981

[51] Int. Cl.³ .................. C12Q 1/34; C12Q 1/38; C12Q 1/36; C13Q 1/12
[52] U.S. Cl. ........................... 435/18; 435/23; 435/24; 435/34; 435/37; 435/871
[58] Field of Search ............ 435/18, 23, 24, 34, 435/37, 871

[56] References Cited

U.S. PATENT DOCUMENTS 4,234,683  11/1980  McMillian .................. 435/18

OTHER PUBLICATIONS

Douglas S. Kellogg, Jr. et al., Applied Microbiology, vol. 25, No. 4, pp. 550-552, 1973.
Sydney M. Finegold et al., Editors, Bailey and Scott's Diagnostic Microbiology Fifth Edition, pp. 142-147; 1978.
Edwin H. Lennette et al., Editors, Manual of Clinical Microbiology, 2nd Edition, pp. 116-129; 1974.

Primary Examiner—Robert J. Warden
Attorney, Agent, or Firm—Warren H. Kintzinger

[57] ABSTRACT

Method for rapid, high intensity visual indication of the presence of Neisseria bacteria species utilizing a new and improved peptone buffer and pH indicator reagent system as the specimen carrier for oxidation series testing, which series test may also include beta lactamase enzyme detection utilizing the reaction of the same reagent system carrying the specimen with a penicillin substrate.

35 Claims, No Drawings

NEISSERIA BACTERIA SPECIES IDENTIFICATION AND BETA LACTAMASE TESTING METHODS

BACKGROUND OF THE INVENTION

Over the years, many systems have been developed for the identification and confirmatory reporting of the existence of certain Neisseria bacteria species. Such testing has become more and more prevalent in more recent years as a result of the increase in the spread of social diseases.

Tests have also been, based on prior research, made for a generation of information relating to resistance or sensitivity of such Neisseria bacteria species to such antibiotics as penicillin or ampicillin. These tests involve subjecting the suspected specimen to a penicillin component, for example, sodium or potassium salts of penicillin G. If the specimen suspension cells possess the beta lactamase enzyme, penicilloic, acid will be produced and the pH indicator in the suspension will change from a red to a yellow color, no color change occurring if the cells do not possess the beta lactamase enzyme.

In connection with the prior art methods of identity testing for such Neisseria bacteria species, three procedures appear to dominate the testing field. The first type of testing is generally referred to as the carbohydrate oxidation test procedures, examples of which are the Cystine Trypticase Soy Agag method (CTSA); Minitek Neisseria test discussed in Hampton, K. D., R. A. Stallings and B. L. Wasilauskas; 1979 comparison of a Slide Coagglutination Technique with the Minitek System for Confirmation of Neisseria gonorrhoeae/J. Clin. Microbiology 10:290–292; the rapid fermentation test discussed in Kellogg D. S. Jr., and E. M. Turner. 1973. Rapid Fermentation Confirmation of Neisseria gonorrhoeae. Applied Microbiol, 25:550–552; and the radioisotope detection of labeled carbohydrates discussed in Strauss, R. R., J. Holderback and H. Friedman, 1978. Comparison of the Radiometric Procedure with Conventional Methods for Identification of Neisseria. J. Clinical Microbiol. 7:419–422.

The second type of tests involve the fluorescent antibody methods of staining individual Neisseria bacteria providing thereby identities of individual species. A third general method is the serological agglutination techniques also used to identify individual species of Neisseria.

One of the shortcomings of utilization of the carbohydrate oxidation type tests is the length of time required for completion of tests.

Since these carbohydrate oxidation tests involve use of visual identification based on color change to indicate the results of the tests, human error may allow color vision defective individuals reading the end results of the tests to make errors. In addition, some of these carbohydrate oxidation tests require an absolutely pure culture or can identify only a single type of Neisseria pathogen or require expensive equipment.

Moreover, as far as can be determined, none of the existing carbohydrate oxidation tests couple visual identification of the presence of Neisseria bacteria species with a beta lactamase enzyme detection test.

SUMMARY OF THE INVENTION

These and other problems, difficulties and disadvantages of the prior art are substantially overcome by the present invention comprising a method for rapid, high intensity, visual identification of the presence of at least five Neisseria bacteria species utilizing a new and improved buffer reagent system including a beef peptone buffer and a pH indicator aqueous solution as a carrier for the suspected specimen. The reagent system carrying the specimen is added to preselected individual carbohydrate substrates to test for the presence of different Neisseria bacteria species. In addition, beta lactamase detection in the specimen may be obtained utilizing the same buffer reagent system carrying the specimen as applied to a penicillin or ampicillin substrate as an indicator of resistance or sensitivity to penicillin and ampicillin antibiotics of the test specimen.

The identification of the presence of the Neisseria bacteria species in the specimen in accordance with the practice of the present invention can be determined by completion of the test results within from about two hours to about seven hours.

The visual indicator identification of positive or negative results of the present invention also is quite simple. If the sample specimen undergoing testing becomes red, Neisseria bacteria species are not present in the specimen. If the specimen undergoing testing turns yellow, the test results are positive and Neisseria bacteria species is present in the resulting specimen.

In accordance with the present invention, an aqueous buffer system reagent comprising a 2% solution of beef peptone, preferably proteose peptones and particularly proteose peptone number 3 is combined with a pH indicator, such as the commonly available phenol red (phenolsolphonophthalein) and the pH of the aqueous buffer solution is maintained in the range of from between 7.1 and about 7.5. This buffer system has admixed therewith NaCl, the reagent including, as the aqueous carrier, distilled water. It is important that the buffer reagent not contain any carbohydrate ingredients. The culture specimen is suspended in the buffer reagent until a dense turpidity results, preferably of a MacFarlane No. 6 level or a greater turpidity is sufficient for purposes of the present invention.

In the testing method of the present invention, the inoculum specimen grown from a pure culture of agar is combined with the buffer reagent and admix therewith to form a suspension.

In preparing the carbohydrates, the four carbohydrates, glucose, maltose, sucrose and lactose, are utilized and coated onto either glass or plastic, individual culture tubes. Each of these coatings are then dried for subsequent use in accordance with the present invention. The dried coated tubes are hereinafter referred to as "substrate" tubes. Reagent grade carbohydrates are used in the practice of the present invention. The carbohydrates are employed in two concentrations, a 5% concentration for maltose and a 20% concentration for each of the glucose, sucrose and lactose carbohydrates. Twenty-five microliters, plus or minus 5 microliters, of each carbohydrate liquid are placed in individual carriers such as disks or tubes and each coated carrier dried after coating with the carbohydrate. These carbohydrates constitute the substrates to be acted upon by the enzymes within the cells of the Neisseria species to be identified. A portion of the suspension of buffer reagent containing the suspect specimen is then added to each of the substrate carriers (here tubes) containing the carbohydrates. The buffer and specimen mixtures are then mixed in the carbohydrate tubes and the tubes placed in a water bath maintained at a temperature of from between 36° C. to about 40° C. After about five minutes, reactions will have occurred indicating whether the test was negative or positive. A color indicates that the test was negative or positive. A red color indicates that the test was negative and a yellow color indicates that the test was positive. An orange color in the tubs indicates an inconclusive test. It is believed that the orange color results from insufficient inoculum or specimen volume in the test tubes.

A fifth test tube may be employed containing either the sodium or potassium salt of penicillin G in order to test for resistance or sensitivity to penicillin or ampicillin of the specimen. To this fifth test tube, a portion of the same buffer reagent solution containing the suspected specimen is added, mixed and let react for about two hours with the buffer reagent and specimen suspension in the fifth test tube at a temperature from between about 36° C. to about 40° C. in a water bath for from between about five minutes to about seven hours (depending upon the reaction state noted during this period). Here again, if the color of the reagent suspension in the fifth test tube turns red, the test is negative, and, if the color of the reagent suspension turns yellow, the test is positive, indicating in the latter case, the presence of a Neisseria bacteria species reactive or resistant to penicillin or ampicillin.

This penicillin resistance or sensitivity test measures beta lactamase production if the specimen is penicillin or ampicillin reactive. A sample of the same buffer-pH indicator reagent containing the specimen used for the carbohydrate testing may be used for the beta lactamase testing as well. In addition, the testing time for beta lactamase production corresponds to the same time frame as the Neisseria bacteria species carbohydrate testing. Moreover, the same color, yellow, identifies beta lactamase production in the fifth test tube.

Thus, simultaneous testing for both Neisseria bacteria species and beta lactamase production can be coupled in accordance with the present invention and the test results reported together.

It is, therefore, an object of the present invention to provide new and improved methods for visual indication of the presence of Neisseria bacteria species.

Another object of the present invention is to provide new and improved methods for rapid, high intensity, visual indication of the presence of Neisseria bacteria species utilizing oxidation series testing procedures.

Still another object of the present invention is to provide new and improved methods for rapid, high intensity, visual indication of the presence of Neisseria bacteria species having a new and improved peptone buffer and pH indicator reagent system as the carrier for the specimen.

A further object of the present invention is to provide new and improved methods for rapid, high intensity, visual indication of the presence of Neisseria bacteria species utilizing a new and improved peptone buffer and pH indicator reagent system as the specimen carrier for carbohydrate oxidation series testing.

A still further object of the present invention is to provide a method for rapid, high intensity, visual indication of the presence of Neisseria bacteria species utilizing a new and improved peptone buffer and pH indicator reagent system as the specimen carrier for carbohydrate oxidation series testing, the testing results for the indication of the presence of a plurality of Neisseria bacteria species being obtainable simultaneously within a short period of time.

Another object of the present invention is to provide new and improved methods for rapid, high intensity, visual indication of the presence of Neisseria bacteria species utilizing a new and improved peptone buffer and pH indicator reagent system as the specimen carrier for carbohydrate oxidation series testing wherein the test results are achieved within from between about five minutes and about seven hours.

Still another object of the present invention is to provide a method for rapid, high intensity, visual indication of the presence of Neisseria bacteria species utilizing a new and improved peptone buffer and pH indicator reagent system as the specimen carrier for carbohydrate oxidation series testing, said series testing providing for such indication of more than one Neisseria bacteria species by a color change indication.

A further object of the present invention is to provide a method for rapid, high intensity, visual indication of the presence of Neisseria bacteria species utilizing a new and improved peptone buffer and pH indicator reagent system as the specimen carrier for carbohydrate oxidation series testing wherein the visual indication is a color indication in which the color yellow indicates a positive reaction in testing a plurality of Neisseria bacteria species suspected specimens.

A still further object of the present invention is to provide for a method for rapid, high intensity, visual indication of the presence of Neisseria bacteria species in a specimen, a new and improved peptone buffer and pH indicator reagent system as the specimen carrier for carbohydrate oxidation series testing, the specimen being premixed with the reagent system prior to testing in the carbohydrate oxidation tests.

Another object of the present invention is to provide such new and improved reagent systems of the immediately preceding object wherein the peptone buffer and pH indicator reagent system admixed with the specimen are in solution form.

Still another object of the present invention is to provide in methods for rapid, high intensity, visual indication of the presence of Neisseria bacteria species in a specimen, a new and improved peptone buffer and pH indicator reagent system as the specimen carrier for carbohydrate oxidation series testing, the pH of the specimen carrier buffer reagent system being maintained in the range of from between about 7.1 and about 7.5.

A further object of the present invention is to provide new and improved beef buffer and pH indicator reagent systems as the specimen carrier for carbohydrate oxidation series testing for the presence of Neisseria bacteria species in the specimen.

A still further object of the present invention is to provide a new and improved beef peptone buffer and pH indicator reagent system for carbohydrate oxidation series testing for the presence of Neisseria bacteria species in the specimen having the pH thereof maintained in the range of from about between 7.1 and about 7.5.

Another object of the present invention is to provide new and improved methods for visual indication of the presence of beta lactamase enzymes in suspected Neisseria bacteria species specimens.

Still another object of the present invention is to provide new and improved methods for rapid, high intensity, visual indication of the presence of beta lactamase in Neisseria bacteria species specimens to determine the resistance or sensitivity of the specimens to penicillin or ampicillin.

A further object of the present invention is to provide new and improved methods for rapid, high intensity, visual indication of the presence of beta lactamase in Neisseria bacteria species specimens utilizing a new and improved peptone buffer and pH indicator reagent system as the carrier for the suspected specimen which is tested for reaction with a penicillin substrate to generate information relating to the resistance or sensitivity of such Neisseria bacteria species specimens to penicillin or ampicillin.

A still further object of the present invention is to provide new and improved methods for rapid, high intensity, visual indication of the presence of beta lactamase in Neisseria bacteria species specimens utilizing a new and improved peptone buffer and pH indicator reagent system as the carrier for the suspected specimen which is tested for reaction with a penicillin substrate to generate information relating to the resistance or sensitivity of such Neisseria bacteria species specimens to penicillin or ampicillin, wherein the test results are obtained within from about 5 minutes to about 7 hours.

Another object of the present invention is to provide new and improved methods for rapid, high intensity, visual indication of the presence of beta lactamase in Neisseria bacteria species specimens utilizing a new and improved peptone buffer and pH indicator reagent system as the carrier for the specimen which is tested for reaction with a penicillin substrate to generate information relating to the existence or sensitivity of such Neisseria bacteria species specimens to penicillin or ampicillin, such visual indication being a color change indication.

Still another object of the present invention is to provide new and improved methods for rapid, high intensity, visual indication of the presence of beta lactamase in Neisseria bacteria species specimens utilizing a new and improved peptone buffer and pH indicator reagent system as the carrier for the suspected specimen which is tested for reaction with a penicillin substrate to generate information relating to resistance or sensitivity of such Neisseria bacteria species specimens to penicillin or ampicillin, the color yellow representing a positive reaction of resistance to penicillin or ampicillin of the specimens.

A further object of the present invention is to provide new and improved methods for rapid, high intensity, visual indication of the presence of beta lactamase in Neisseria bacteria species specimens utilizing a new and improved peptone buffer and pH indicator reagent system as the carrier for the suspected specimen for oxidation series testing, which specimen carrying reagent system may also be employed for detection of resistance or sensitivity of the specimen to penicillin or ampicillin.

A still further object of the present invention is to provide new and improved methods in accordance with the immediately preceding object wherein the reaction results of the testing for the presence of a Neisseria bacteria species and of beta lactamase occur with the same time frame reference and with positive indications for both type testing exhibiting the same color.

These and other objects, features and advantages of the present invention will become readily apparent to one skilled in the art from a careful consideration of the following detailed description and the examples set forth herein.

PREFERRED EMBODIMENTS OF THE INVENTIONS

Five Neisseria species of bacteria, namely, *gonorhoeae, meningitidis, lactamica, sicca* and *catarrhalis* (now commonly called *Branhamella catarrhalis*), have been successfully tested in accordance with the practice of the present invention as more fully explained hereinafter.

In general, the methods of the present invention involve mixing a specimen of the suspected bacteria with a pre-prepared liquid peptone buffer and pH indicator reagent system of the present invention to form a liquid suspension which is then contacted with certain carbohydrates, namely, glucose, maltose, sucrose and lactose. The resulting solution is mixed to permit reaction of the Neisseria bacteria species with the carbohydrate, over a relatively short time. If the test results exhibit a red color, then the suspect specimen is negative and does not contain the Neisseria bacteria species, for which the test was conducted. If, on the other hand, the reaction product exhibits a yellow color, the test is positive, indicating the type of the Neisseria bacteria species present for which the test was being conducted.

The carbohydrate testing is completed quite rapidly, with a time period of from between about five minutes and about seven hours. The positive visual indication of the presence of the Neisseria bacteria species being tested for is of a high intensity yellow color.

The increased rapidity of reaction is attributable to the unique beef peptone buffering-pH indicator reagent system of the present invention employing a predetermined pH level. In general, proteose peptones and in particular, proteose peptone number 3, sold under that designation by Difco Laboratories, Inc. of Detroit, Michigan, have been found particularly useful in the formulation of the peptone buffer-pH indicator reagent system. The commonly used pH indicator, phenol red, is used in the formulation of the peptone buffer-pH indicator reagent system of the present invention. The reagent system involves adding the peptone, for example, peptone number 3, in an amount of from about 1.5% to about 2.5% by volume of the phenol red. When mixed with the beef peptone, the final concentration of phenol red in the reagent system is from about 0.04 to about 0.085 grams per liter. At these concentrations of the phenol red in the reagent system, the negative and positive colors of the resultant reactant solution of the carbohydrate testing are visually enhanced considerably. It is noted that with these concentrations, the toxicity effects due to the presence of phenol red is substantially minimized. Thus, readability of the test results is considerably enhanced by virtue of the pH indicator concentration in the reagent system. It is also important that the pH of the reagent system be maintained within a pH range of from between about 7.1 and about 7.5 to provide effective buffering. Sodium chloride is added for pH control and the carrier for the reagent system is distilled water.

The carbohydrate substrates to be acted upon by enzymes within the cells of the Neisseria bacteria species to be identified are glucose, maltose, sucrose and lactose. The carbohydrates are separately placed in individual glass or plastic tubes and dried or placed on paper disks or strips and dried. These carbohydrates in the tests conducted in the practice of the present invention are in two concentrations, a 5% concentration of maltose and a 20% concentration for each of glucose, sucrose and lactose. While the above percentage concentrations are preferable, concentrations of maltose of from between about 1% and about 5%, and concentrations of glucose, sucrose and lactose may be employed in the practice of the present invention, each in an amount of from between about 5% and about 20%.

From between about 20 microliters and about 30 microliters of each carbohydrate is placed in a separate tube for drying. Experience has indicated that after drying, these carbohydrates can be stored and are stable for test purposes for up to about one full year. Reagent grade carbohydrates only are used in the tests according to the present invention.

The Neisseria bacteria species, particularly identified above, produce acid reactions only with certain of these carbohydrates. It appears the acid reaction between the particular bacteria and the carbohydrates in the carbohydrate substrate tube (after addition of the specimen carrying beef peptone-pH indicator reagent system to the carbohydrate substrate tube) results in the lowering of the pH of the mixture in the substrate tube, thereby turning the pH indicator from a red color to a yellow color. Such change to yellow indicates the presence of the Neisseria bacteria species being investigated.

As specific examples of specimen carrier beef peptone-pH indicator reagent systems of the present invention, various reagent systems were formulated. In one series of formulations, a 1.5% solution of proteose peptone was mixed with 0.04 grams per liter of phenol red in distilled water. Sodium chloride was added in an amount sufficient to maintain the reagent system with a pH in the range of from between about 7.1 and about 7.5.

In another series of formulations, the reagent system was formulated with a 2.5% solution of proteose peptone mixed with about 0.085 grams per liter of phenol red in distilled water. The pH in thise series of formulations was also controlled by NaCL addition so that the pH range of the reagent system was from between about 7.1 to about 7.5.

Another series of formulations of the reagent system included 20 grams per liter of proteose peptone number 3 mixed with from between about 0.4 grams per liter and about 0.85 grams per liter of phenol red. Five grams per liter of sodium chloride was added to produce a resultant buffer reagent system pH of from between about 7.1 to about 7.5.

The carbohydrate substrates were prepared as follows. In one series of formulation of carbohydrate substrates, about 1% of maltose was added to a test tube and dried and about 5% of glucose was added to another tube, 5% sucrose added to a third tube, and about 5% added to a fourth test tube, thesse latter tubes also being dried.

In another series of formulations, 5% of maltose was added to a test tube and 20% of glucose, sucrose and lactose was added separately to individual test tubes and dried. Reagent grade carbohydrates only were used, and after drying, the carbohydrates were found to be storage stable for about one full year.

The Neisseria bacteria species cells are incubated on culture plates and are scraped from the plates and added to the reagent system tubes until a dense turpidity results. A MacFarlane number 6 or greater turpidity was found sufficient for correct identifications in the tests performed in accordance with the present invention. The Neisseria bacteria species cells are scraped from the surface of the culture plate and suspended in the reagent system tube. This cell suspension specimen carrier reagent system is then added to the carbohydrate substrate tubes. It has been found that four drops from a Pasteur pippete are usually sufficient for test purposes. After the specimen carrying beef peptone buffer-pH indicator reagent system has been added to and mixed with the carbohydrate substrate tubes, the mixtures in the substrate tubes are incubated at a temperature of from between about 36° C. to about 40° C. in a water bath. The mixtures are permitted to incubate for from beteween about 5 minutes to about 7 hours, depending upon the rapidity of the reactions.

In the methods of the present invention, the red color indicates that the particular test is negative, whereas a yellow color in the substrate tube indicates a positive reaction evidencing the presence of the Neisseria bacteria species.

Table 1 is a graphical illustration of the simultaneous testing for the identified Neisseria bacteria species with the plus sign indicating a yellow positive visual indication and the negative sign indicating a negative visual indication.

TABLE 1

|  | Glucose | Maltose | Sucrose | Lactose |
|---|---|---|---|---|
| N. gonorrhoeae | + | − | − | − |
| N. meningitidis | + | + | − | − |
| N. lactamica | + | + | − | + |
| N. sicca | + | + | + | − |
| N. catarrhalis (Branhamella) | − | − | − | − |

As a control, the aforementioned CTA test was employed and of over 450 cultures tested for the presence of Neisseria bacteria species in accordance with the present invention, more that 98% agreement existed with the CTA control tests. It will be appreciated that there is a considerable time savings in the practice of the present invention in both setting up of the test procedures and in the turn around time for producing test results. In addition, simultaneous testing for different Neisseria bacteria species is possible with the same specimen carrying peptone buffer-pH indicator reagent system of the present invention being used for testing of the different Neisseria bacteria species.

Unexpectedly, it was found that the methods of the present invention for visual identification of Neisseria bacteria species can be coupled with beta lactamase testing of suspected specimens for resistance or sensitivity to penicillin or ampicillin utilizing the same proteose peptone buffer-pH indicator reagent system utilized in the carbohydrate oxidation tests. In addition, the test for beta lactamase can be conducted simultaneously with the carbohydrate oxidation identification tests within the same time reference and with the same yellow color indicating a positive beta lactamase reaction.

For purposes of beta lactamase production, a sodium or potassium salt of penicillin G is used as a substrate. An aqueous solution of from between about 1% and about 5% of sodium or potassium salt of penicillin G is absorbed on paper disks and dried rapidly. After drying, these disks are stored in dessicant at from between about 2° C. to about 8° C. in a tightly covered container. It has been found that these beta lactamase substrates, when dried on the paper disks, are stored stable for about 6 months at a refrigerated temperature of from between about 2° C. and about 8° C. and storage stable for about 1 year if frozen in a non-frost free freezer.

For the beta lactamase enzyme test, the dried penicillin G salt containing disk is placed in a fifth clean test tube to which is added 3 or 4 drops of the specimen carrying proteose peptone buffer-pH indicator reagent system used in the carbohydrate oxidation tests. The reagent system and penicillin containing disks are stirred in the fifth test tube and, like the carbohydrate oxidation test mixtures, are incubated at from between about 36° C. and about 40° C. in a water bath for from between about 5 minutes and about 7 hours. If the fifth test tube during this time frame exhibits a red color, then the test for the presence of the beta lactamase enzyme is negative. If the color of the fifth test tube turns yellow, the color of the reaction product in the fifth test tube is positive, indicating the presence of the beta lactamase enzyme and the possibility of resistance to penicillin or ampicillin.

It will, therefore, be appreciated that, by employment of the peptone buffer-pH indicator reagent system of the present invention, both testing for carbohydrate oxidation and beta lactamase existence can be simultaneously and rapidly visually indicated with the same color indicating positive reactions of both the existence of particular Neisseria bacteria species and beta lactamase enzymes in the specimen undergoing tests.

While specific embodiments have been disclosed and described in the specifications and examples above, it will be understood that the present inventions desired to be protected are found therein and within the scope of the following claims.

I claim:

1. A method for providing rapid, high intensity, visual indication of the presence of Neisseria bacteria species in a specimen comprising: the steps of admixing the specimen with a peptone buffer and pH indicator reagent system to form a specimen suspension, contacting the reagent system specimen suspension with at least one carbohydrate substrate taken from the class consisting of glucose, maltose, sucrose and lactose, permitting the reagent system specimen to react with the contacted carbohydrate substrate, and visually observing the reaction results for color change in a predetermined time period.

2. The method of claim 1 wherein a portion of the reagent system specimen suspension is contacted with each of said carbohydrate substrates for reaction of the reagent system specimen with the contacted carbohydrate substrate for visual observation of the reaction results for color change.

3. The method of claim 1 wherein the reaction results are visually observed within a time period of from between about two hours and about seven hours for color change.

4. The method of claim 3 wherein a color change to a yellow color indicates the presence of Neisseria bacteria species in the specimen.

5. The method of claim 4 wherein the Neisseria bacteria species undergoing testing is taken from the class consisting of N. gonorrhoeae, N. meningitidis, N. lactamica, N. sicca and N. catarrhalis.

6. The method of claim 1 wherein the peptone buffer and pH indicator reagent system has a pH within the range between about 7.1 and about 7.5.

7. The method of claim 6 wherein the peptone buffer is a proteose peptone material.

8. The method of claim 7 wherein the proteose peptone buffer is a beef peptone material.

9. The method of claim 8 wherein the proteose beef peptone buffer is peptone number 3.

10. The method of claim 7 wherein the proteose peptone is present in the reagent system in an amount of from between about 1.5% to about 2.5% by volume.

11. The method of claim 7 wherein the pH indicator is phenol red.

12. The method of claim 10 wherein the pH indicator is phenol red and is present in said aqueous reagent system in an amount of from between about 0.04 and about 0.085 grams per liter.

13. The method of rapid, high intensity, visual indication of the presence of beta lactamase enzymes in a specimen comprising the steps of admixing the specimen with a peptone buffer and pH indicator reagent system to form a specimen suspension, contacting the reagent system specimen suspension with a penicillin substrate, permitting the reagent system specimen to react with the contact penicillin substrate, and visually observing the reaction results for color change in a predetermined time period.

14. The method of claim 13 wherein the penicillin substrate is a salt of penicillin and the reaction results are visually observed within a time period of from between about five minutes and about seven hours for color change.

15. The method of claim 14 wherein the penicillin salt is taken from the class consisting of sodium and potassium penicillin G and wherein a color change to a yellow color indicates the presence of beta lactamase enzyme in the specimen.

16. The method of claim 15 wherein the Neisseria bacteria species undergoing testing is taken from the class consisting of N. gonorrhoeae, N. meningitidis, N. lactamica, N. sicca and N. catarrhalis.

17. The method of claim 13 wherein the peptone buffer and pH indicator reagent system has a pH within the range between about 7.1 and about 7.5.

18. The method of claim 17 wherein the peptone buffer is a proteose peptone material.

19. The method of claim 18 wherein the proteose peptone buffer is a beef peptone material.

20. The method of claim 19 wherein the proteose beef peptone buffer is peptone number 3.

21. The method of claim 18 wherein the proteose peptone is present in the reagent system in an amount of from between about 1.5% to about 2.5% by volume.

22. The method of claim 18 wherein the pH indicator is phenol red.

23. The method of claim 21 wherein the pH indicator is phenol red and is present in said aqueous reagent system in an amount of from between about 0.04 and about 0.085 grams per liter.

24. A method of rapid, high intensity, visual indication of the presence of Neisseria bacteria species and of beta lactamase enzyme in a specimen comprising the steps of admixing the specimen with a peptone buffer and pH indicator reagent system to form a specimen suspension, which is contacted with a penicillin substrate, and with carbohydrate substrates separately, permitting the reagent system specimen to react with the contacted carbohydrate substrates and the penicillin substrate, and visually observing the reaction results for color change induced by the presence of one or more enzymes taken from the class consisting of N. gonorrhoeae, N. meningitidis, N. lactamica, and N. sicca, in a predetermined time period.

25. The method of claim 25 wherein a portion of the reagent system specimen suspension is contacted with each of said carbohydrate substrates for reaction of the reagent system specimen with the contacted carbohydrate substrate for visual observation of the reaction results for color change.

26. The method of claim 24 wherein the reaction results are visually observed within a time perod of from between about two hours and about seven hours for color change.

27. The method of claim 26 wherein color change to a yellow color indicates the presence of Neisseria bacteria species and beta lactamase in the specimen.

28. The method of claim 27 wherein the Neisseria bacteria species undergoing testing is taken from the class consisting of *N. gonorrhoeae, N. meningitidis, N. lactamica, N. sicca* and *N. catarrhalis.*

29. The method of claim 24 wherein the peptone buffer and pH indicator reagent system has a pH within the range between about 7.1 and about 7.5.

30. The method of claim 29 wherein the peptone buffer is a proteose peptone material.

31. The method of claim 30 wherein the proteose peptone buffer is a beef peptone material.

32. The method of claim 31 wherein the proteose beef peptone buffer is peptone number 3.

33. The method of claim 30 wherein the proteose peptone is present in the reagent system in an amount of from between about 1.5% to about 2.5% by volume.

34. The method of claim 30 wherein the pH indicator is phenol red.

35. The method of claim 33 wherein the pH indicator is phenol red and is present in said aqueous reagent system in an amount of from between about 0.04 and about 0.085 grams per liter.

* * * * *